US00PP31514P2

(12) United States Plant Patent
Van Swieten

(10) Patent No.: US PP31,514 P2
(45) Date of Patent: Mar. 3, 2020

(54) ***PHALAENOPSIS* ORCHID PLANT NAMED 'PHALFEWYP'**

(50) Latin Name: ***Phalaenopsis* hybrid**
Varietal Denomination: PHALFEWYP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,156

(22) Filed: Feb. 26, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

(56) References Cited

PUBLICATIONS

EU Community Plant Variety Rights Application No. 2017/1135, Application n°A201701175, filed Apr. 25, 2017, 8 pages.
EU Community Plant Variety Office Official Gazette, 3.2017, Jun. 15, 2017, cover page and pp. 37, 57.
EU Community Plant Variety Rights Certificate on the Grant, EU 50195, Sep. 10, 2018, 2 pages.
EU Community Plant Variety Office Official Gazette, 6.2018, Dec. 15, 2018, cover page and p. 79.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALFEWYP', particularly characterized by having reddish-purple flowers with small, very light purple centers and red-purple lips, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFEWYP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFEWYP'.

The new *Phalaenopsis* plant is a product of a planned breeding program conducted by the inventor in Bleiswijk, The Netherlands. The objective of this breeding program was to create a new *Phalaenopsis* plant with numerous attractive, reddish-purple flowers with small, very light purple centers and red-purple lips, suitable for potted plant production.

The new *Phalaenopsis* plant 'PHALFEWYP' is a result of cross-pollination made by the inventor in August 2006 in Bleiswijk, The Netherlands, of the proprietary female, or seed parent, *Phalaenopsis* hybrid '23426-01' (unpatented) with the proprietary male, or pollen parent, *Phalaenopsis* hybrid '14261-01' (unpatented).

The new *Phalaenopsis* was selected by the inventor as a single plant within the progeny of the stated cross-pollination in a controlled greenhouse in Bleiswijk, The Netherlands, in August 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017, by Applicant who obtained the subject matter disclosed directly from the Inventor. 'PHALFEWYP' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALFEWYP' as a new and distinct variety of *Phalaenopsis* plant:

1) Reddish-purple flowers with small, very light purple centers and red-purple lips;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week-old plants in December 2018. Colors in the photographs may differ from the color values cited in the detailed botanical description, which accurately describe the actual colors of the new variety.

DESCRIPTION OF THE NEW VARIETY

Figure 1:
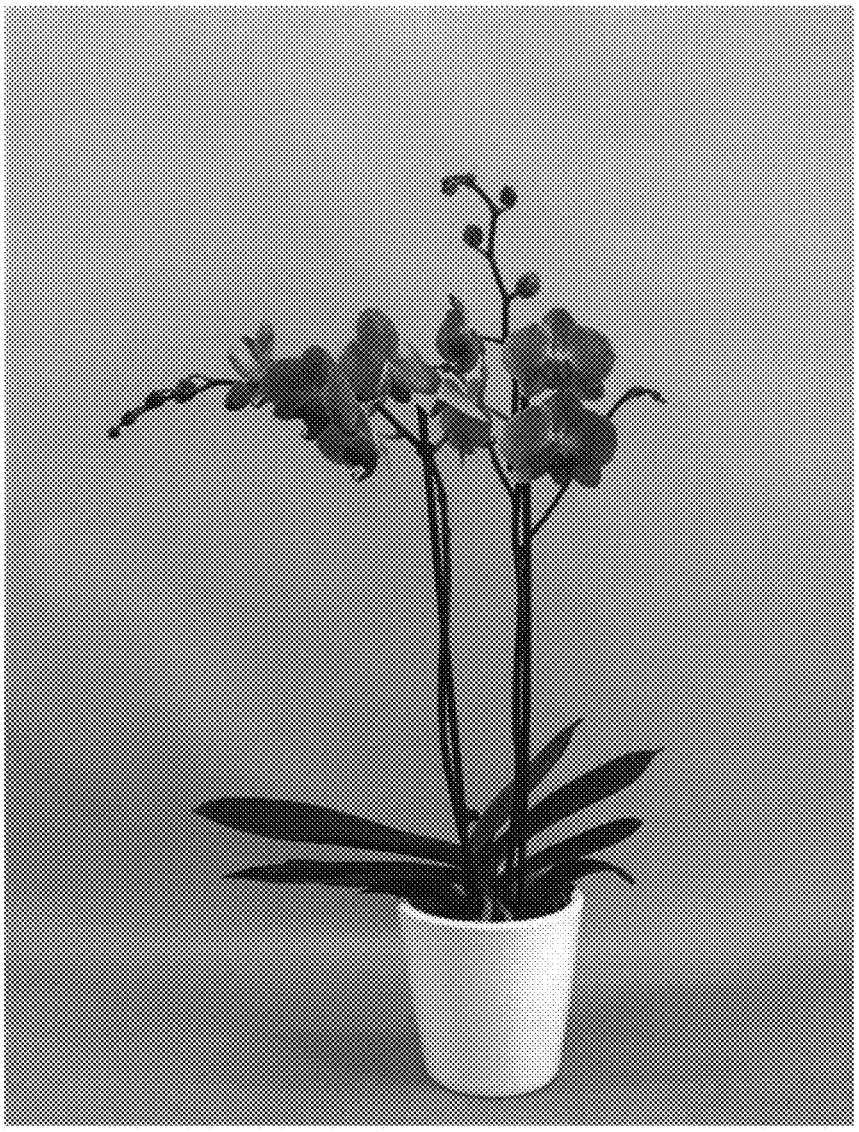
FIG. 1 shows the overall plant habit, including blooms, buds and foliage of 'PHALFEWYP'.
Figure 2:
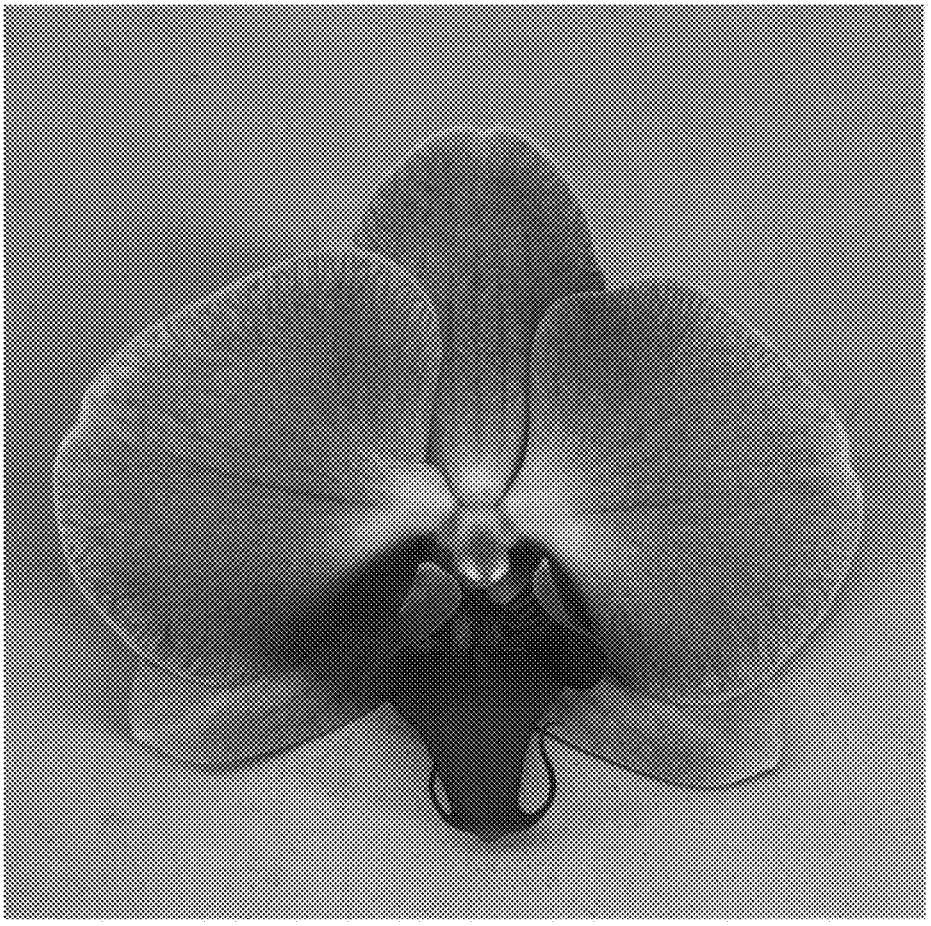
FIG. 2 shows a close-up of a flower of 'PHALFEWYP'.
Figure 3:
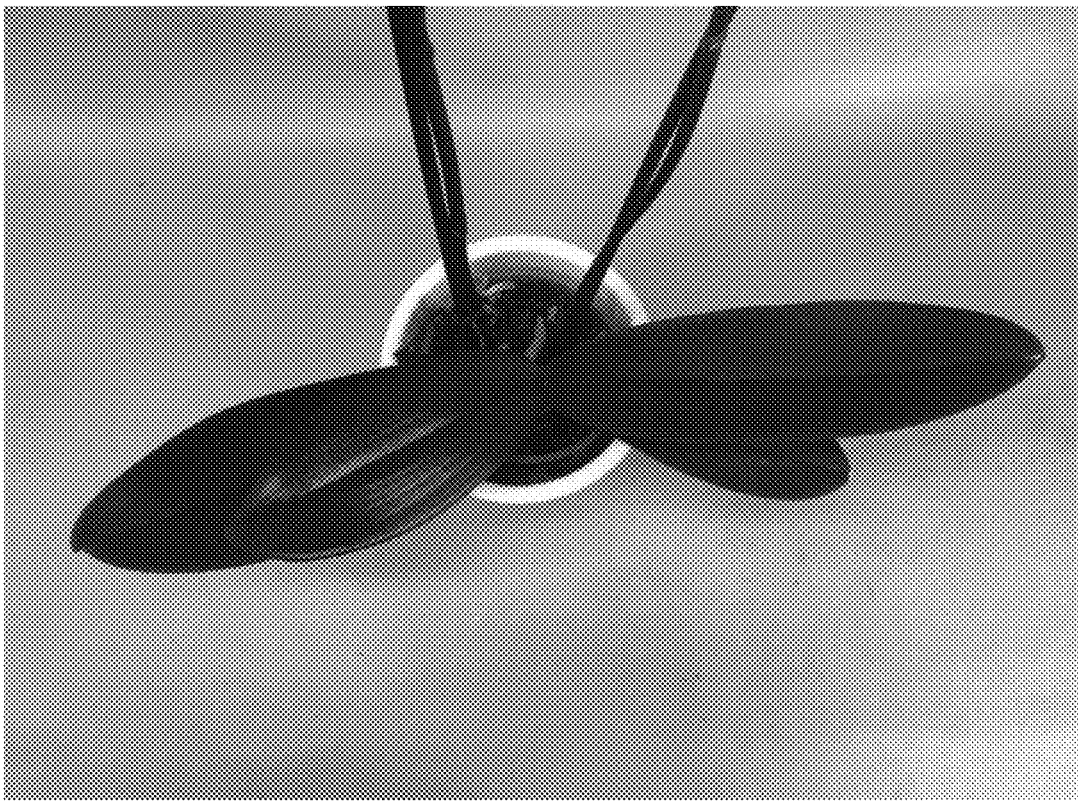
FIG. 3 shows an overhead view of the leaves of 'PHALFEWYP'.

The following detailed description sets forth the distinctive characteristics of 'PHALFEWYP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in December 2018 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFEWYP'.

Parentage:

*Female parent*.—*Phalaenopsis* cultivar '23426-01' (unpatented).

*Male parent*.—*Phalaenopsis* cultivar '14261-01' (Unpatented).

Propagation:

*Type*.—Meristem tissue culture.

Roots:

*Root description*.—Greyed-green (between RHS 190B and 190C) colored roots with branching lateral roots having purplish-red (RHS N77B) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme to panicle inflorescence.

*Height (from soil level to top of inflorescence)*.—Approximately 55.0 cm to 65.0 cm.

*Width (measured from leaf tips)*.—About 31.0 cm to 36.0 cm.

*Vigor*.—Moderate.

Leaves:

*Mature leaves*.—Quantity per plant: 6 to 8 leaves are produced before flowering. Length (fully expanded): 20.0 cm to 23.0 cm. Width: 7.5 cm to 8.5 cm. Shape: Oblong. Base shape: Moderately elongated. Apex: Obtuse to acute unequal. Leaf blade angle with the petiole (measured from the horizontal position): Between 30 degrees and 40 degrees. Leaf margin: Entire. Color: Upper surface: RHS 146A. Lower surface: RHS 146B and RHS N186C. Texture (upper surface): Rough. Texture (lower surface): Smooth. Thickness: 2.5 mm to 2.8 mm. Venation: Pattern: Parallel. Color of the midvein: Upper surface: RHS 146A. Lower surface: RHS N186C.

Peduncle:

*Quantity per plant*.—1 to 2.

*Number of flowers per peduncle*.—10 to 16.

*Length*.—55.0 cm to 65.0 cm.

*Diameter*.—5.0 mm to 6.0 mm.

*Strength*.—Strong.

*Aspect*.—Upright to slightly pendant.

*Texture*.—Smooth.

*Color*.—Mix of brown (RHS 200B) and green (RHS 146C).

*Internode length*.—3.0 cm to 4.0 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 190.0 mm to 240.0 mm. Diameter: 120.0 mm to 140.0 mm.

*Flowering time*.—First flowers can be expected 10 to 11 months after planting in a 12-cm pot.

*Flower*.—Height: 80.0 mm to 85.0 mm. Diameter: 100.0 mm to 105.0 mm. Depth of lip: 26.0 mm to 28.0 mm.

*Flower longevity*.—On the plant: 12 to 17 weeks.

*Fragrance*.—Absent.

*Flower bud*.—Average size: Large. Length: 23.0 mm to 25.0 mm. Width: 19.0 mm to 21.0 mm. Shape: Egg shaped. Color: Purplish-red (RHS N77B) with a touch of dark purplish-red (RHS N186D).

*Petals*.—Arrangement: Open/free. Shape: Semi-circular. Apex: Emarginated asymmetric. Margin: Slightly undulated. Length (from base to tip): 45.0 mm to 47.0 mm. Width: 56.0 mm to 58.0 mm. Color (when fully opened): Upper surface: Basic color: Reddish-purple (RHS N78B). Over color: Small, very light purple center (RHS 76B). Lower surface: Basic color: Light reddish-purple (RHS N78D). Over color: Reddish-purple (RHS N78B) toward margin.

*Dorsal sepal*.—Shape: Elliptic. Apex: Emarginated symmetric. Margin: Entire. Length (from base to tip): 46.0 mm to 48.0 mm. Width: 31.0 mm to 33.0 mm. Color (when fully opened): Upper surface: Basic color: Reddish-purple (RHS N78B). Over color: Slightly very light purple center (RHS 76B). Lower surface: Basic color: Reddish-purple (RHS N78B). Over color: Light red-purple (RHS N78D) toward apex.

*Lateral sepals*.—Shape: Ovate. Apex: Obtuse asymmetric. Margin: Entire. Length (from base to tip): 46.0 mm to 48.0 mm. Width: 28.0 mm to 30.0 mm.

Color (when fully opened): Upper surface: Basic color: Reddish-purple (between RHS N78B and N78C). Over color: Slightly light green (RHS 195B) at the base with few purplish-red spots (RHS 185C) and light purple apex (RHS 76B). Lower surface: Basic color: Reddish-purple (RHS N78B). Over color: Slightly light green (RHS 195A) at the base.

*Labellum* (*lip*).—Whiskers: Present. Length of whiskers: 14.0 mm to 16.0 mm. Color of whiskers: Purplish-red (RHS 71A). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 20.0 mm to 22.0 mm. Width: 15.0 mm to 17.0 mm. Color: Upper surface: White (RHS NN155C) with purplish-red stripes (RHS 59B) at the base; dark red (RHS 59A) on one side; reddish-purple (RHS N78A) toward other side. Lower surface: White (RHS NN155C) at the base; dark red (RHS 59A) on one side and reddish-purple (RHS N78A) toward the front.

*Apical lobe*.—Shape: Triangular. Margin: Entire. Length: 21.0 mm to 23.0 mm. Width: 20.0 mm to 22.0 mm. Color: Upper surface: Dark red wings (RHS 59A) and reddish-purple (RHS N78A) toward whiskers. Lower surface: Dark red wings (RHS 59A); light purple (RHS 76A) in the middle from the base toward the whiskers; reddish-purple (RHS N78A) toward the margin.

*Callus*.—Average size: Medium. Height: 6.0 mm to 7.0 mm. Length: 5.0 mm to 6.0 mm. Width: 4.0 mm to 5.0 mm. Color: Yellow (RHS 8A); dotted (RHS 59B).

Reproductive organs:

*Column*.—Length: 8.0 mm to 10.0 mm. Diameter: 5.1 mm to 5.4 mm. Color: Light purple (RHS 76A) at the base; reddish-purple (RHS N78B) toward the tip.

*Pollinia*.—Quantity: 2. Diameter: 0.8 mm to 1.0 mm. Color: Orange-yellow (RHS 23A).

*Ovary*.—Length: 11.0 mm to 13.0 mm. Diameter: 1.9 mm to 2.3 mm. Color: Light green (RHS 195B) and very light purple (RHS 76B) toward the flower.

*Pedicel*.—Length: 39.0 mm to 41.0 mm. Diameter: 2.4 mm to 3.1 mm. Color: Slightly purplish-red (RHS N77B) at the base; light green (RHS 195B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFEWYP' differs from female parent plant '23426-01' (unpatented) in that 'PHALFEWYP' has purplish-red whiskers, whereas '23426-01' has purplish-pink whiskers with light yellow tips. Additionally, 'PHALFEWYP' has larger flowers and shorter whiskers than '23426-01'.

'PHALFEWYP' differs from male parent plant '14261-01' (unpatented) in that 'PHALFEWYP' has reddish-purple flowers and purplish-red (RHS 71A) whiskers, whereas '14261-01' has very light purple flowers and dark purplish-red (RHS N79C) whiskers. Additionally, 'PHALFEWYP' has larger flowers and shorter whiskers than '14261-01'.

'PHALFEWYP' is most similar to the commercial *Phalaenopsis* plants named 'PHALCIMEI' (U.S. Plant Pat. No. 27,200) and 'PHALDESBIM' (U.S. Plant Pat. No. 27,671). 'PHALFEWYP' differs from the commercial variety 'PHALCIMEI' in that 'PHALFEWYP' has purplish-red (RHS 71A) whiskers and slightly undulated petal margins, whereas 'PHALCIMEI' has purplish-red (RHS 60B) whiskers with white tips and entire petal margins. Additionally, 'PHALFEWYP' has shorter whiskers and shorter dorsal sepals than 'PHALCIMEI'.

'PHALFEWYP' differs from the commercial variety 'PHALDESBIM' in that 'PHALFEWYP' has slightly undulated petal margins, whereas 'PHALDESBIM' has entire petal margins. Additionally, 'PHALFEWYP' has longer dorsal sepals than 'PHALDESBIM'.

I claim:

1. A new and distinct variety of *Phalaenopsis* plant named 'PHALFEWYP', substantially as described and illustrated herein.

* * * * *